(12) United States Patent
Kuo et al.

(10) Patent No.: US 7,235,659 B2
(45) Date of Patent: Jun. 26, 2007

(54) PROCESS FOR PREPARING SUBSTITUTED 5-AMINO-PYRAZOLO-[4,3-E]-1,2,4-TRIAZOLO[1,5-C]PYRIMIDINES

(75) Inventors: Shen-Chun Kuo, Union, NJ (US); Loc Thanh Tran, Piscataway, NJ (US); Pengyi Zhang, Clark, NJ (US)

(73) Assignee: Schering Corporation, Kenilworth, NJ (US)

( * ) Notice: Subject to any disclaimer, the term of this patent is extended or adjusted under 35 U.S.C. 154(b) by 319 days.

(21) Appl. No.: 10/999,048

(22) Filed: Nov. 29, 2004

(65) Prior Publication Data

US 2006/0149060 A1 Jul. 6, 2006

Related U.S. Application Data

(60) Provisional application No. 60/525,925, filed on Dec. 1, 2003.

(51) Int. Cl.
*C07D 239/00* (2006.01)
(52) U.S. Cl. ..................................................... 544/251
(58) Field of Classification Search ................... None
See application file for complete search history.

(56) References Cited

FOREIGN PATENT DOCUMENTS

WO WO 95/01356 1/1995
WO WO 01/92264 A1 12/2001

OTHER PUBLICATIONS

Baraldi, Pier Giovanni, et al., "Design, Synthesis, and Biological Evaluation . . . ," J. Med. Chem. 46: 1229-1241 (2003).

*Primary Examiner*—Zachary C. Tucker
*Assistant Examiner*—Erich A. Leeser

(57) ABSTRACT

A process for preparing substituted 5-amino-pyrazolo[4,3-e]-1,2,4-triazolo-[1,5-c]pyrimidine compounds having an aminoalkyl substituent at the 7-position is disclosed.

26 Claims, No Drawings

PROCESS FOR PREPARING SUBSTITUTED 5-AMINO-PYRAZOLO-[4,3-E]-1,2,4-TRIAZOLO[1,5-C]PYRIMIDINES

This application claims the benefit of priority of U.S. Ser. No. 60/525,925, filed Dec. 1, 2003.

FIELD OF THE INVENTION

The present invention relates to a process for preparing substituted 5-amino-pyrazolo[4,3-e]-1,2,4-triazolo-[1,5-c]pyrimidine compounds having an aminoalkyl substituent at the 7-position.

BACKGROUND

Substituted 5-amino-pyrazolo[4,3-e]-1,2,4-triazolo-[1,5-c]pyrimidine compounds disclosed in WO 01/92264 are useful as $A_{2a}$ receptor antagonists in the treatment of central nervous system diseases, in particular Parkinson's disease.

WO 01/92264 discloses processes for preparing 5-amino-2-substituted-pyrazolo[4,3-e]-1,2,4-triazolo-[1,5-c]pyrimidines comprising dehydrative rearrangement of hydrazines.

SUMMARY OF THE INVENTION

The present invention relates to a process for preparing compounds of formula 7

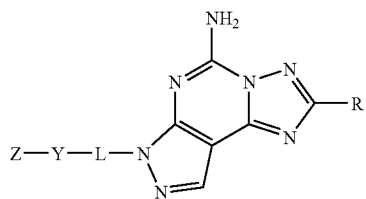

formula 7 or a pharmaceutically acceptable salt or solvate thereof, wherein

L is alkylene;

R is aryl, heteroaryl, $R^1$-aryl, $R^1$-heteroaryl or cycloalkenyl;

Y is —N($R^2$)CH$_2$CH$_2$N($R^3$)—, —OCH$_2$CH$_2$N($R^2$)—, —(CH$_2$)$_2$—NH—, or

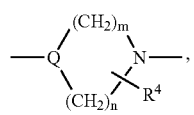

and

Z is aryl, $R^5$-aryl, aralkyl, $R^5$-aralkyl, heteroaryl, $R^5$-heteroaryl, (aryl)$_2$alkyl-, $R^6$—C(O)—, C(O)—, $R^6$—SO$_2$—,

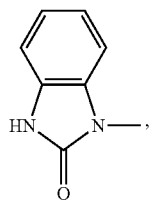

$R^5$-aryl-CH(OH)—; or aryl-CH(OH)—; or when Q is

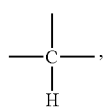

Z is also phenylamino or pyridylamino;

or

Z and Y together are

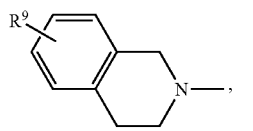

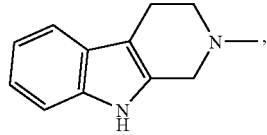

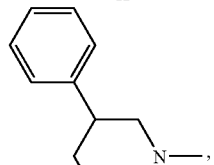

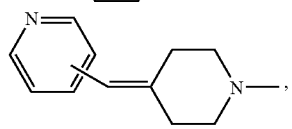

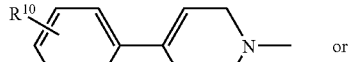 or

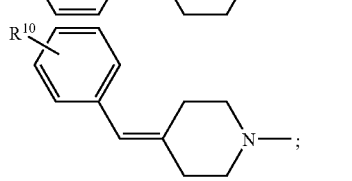

$R^1$ is 1 to 3 substituents independently selected from the group consisting of hydrogen, alkyl, —CF$_3$, halogen, —NO$_2$, —NR$^{12}$R$^{13}$, alkoxy, alkylthio, alkylsulfinyl, and alkylsulfonyl;

$R^2$ and $R^3$ are independently selected from the group consisting of hydrogen and alkyl;

m and n are each independently 2 or 3;

Q is

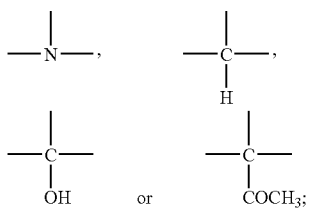

$R^4$ is 1 to 2 substituents independently selected from the group consisting of hydrogen and alkyl, or two $R^4$ substituents on the same carbon can form =O;

$R^5$ is 1 to 5 substituents independently selected from the group consisting of hydrogen, halogen, alkyl, hydroxy, alkoxy, —CN, dialkyl-amino, —CF$_3$, —OCF$_3$, acetyl, —NO$_2$, hydroxyalkoxy, alkoxyalkoxy, dialkoxy-alkoxy, alkoxy-alkoxy-alkoxy, carboxy-alkoxy, alkoxycarbonyla-lkoxy, cycloalkyl-alkoxy, dialkyl-amino-alkoxy, morpholinyl, alkyl-SO$_2$—, alkyl-SO$_2$-alkoxy, tetrahydropyranyloxy, alkylcarbonyl-alkoxy, alkoxycarbonyl, alkylcarbonyloxy-alkoxy, —SO$_2$NH$_2$, or phenoxy; or adjacent $R^5$ substituents together are —O—CH$_2$—O—, —O—CH$_2$CH$_2$—O—, —O—CF$_2$—O— or —O—CF$_2$—O— and form a ring with the carbon atoms to which they are attached;

$R^6$ is alkyl, aryl, $R^5$-aryl, aralkyl, $R^5$-aralkyl, heteroaryl, $R^5$-heteroaryl, $R^5$-cycloalkyl, cycloalkyl, alkyl-OC(O)—NH—(C$_1$–C$_6$)alkyl-, dialkyl-aminomethyl or

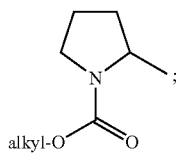

$R^9$ is 1 to 2 substituents independently selected from the group consisting of hydrogen, alkyl, hydroxy, alkoxy, halogen, —CF$_3$ and alkoxy-alkoxy;

$R^{10}$ is 1 to 5 substituents independently selected from the group consisting of hydrogen, halogen, alkyl, hydroxy, alkoxy, —CN, —NH$_2$, alkylamino, dialkylamino, —CF$_3$, —OCF$_3$ and —S(O)$_{0-2}$alkyl;

$R^{12}$ is hydrogen or alkyl;

and $R^{13}$ is alkyl-C(O)— or alkyl-SO$_2$—;

comprising a) halogenating and formylating a compound of formula 6

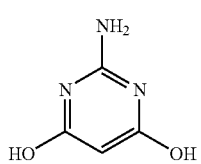

to obtain a compound of formula 5

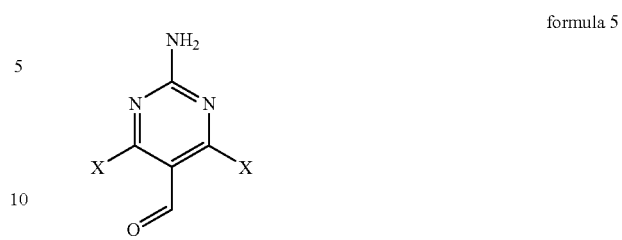

wherein X is halogen (b) coupling the compound of formula 5 with a hydrazine of formula 4

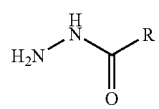

in the presence of a base to form a compound of formula 3

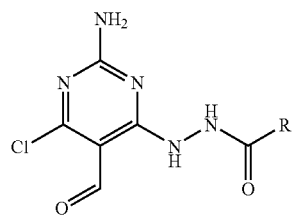

(c) reacting the compound of formula 3 with a compound of formula HO-L-NHNH$_2$ to form a compound of formula 2

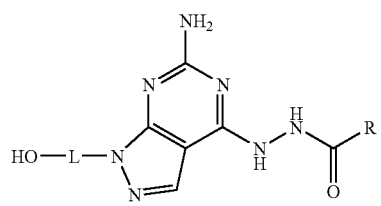

(d) concurrently (1) cyclizing and (2) halogenating the compound of formula 2 by reacting the compound of formula 2 in the presence of catalytic amount of a metal halide or a catalytic amount of a halide salt and a dehydrating agent to form a compound of formula 1

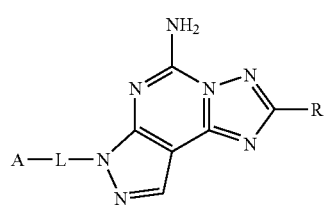

wherein A is halogen;

and (e) preparing the compound of formula 7 by coupling the compound of formula 1 with a compound of formula 8

Z-Y—H formula 8 in the presence of a base.

In particular, the invention relates to the cyclizing and halogenation of a compound of formula 1, along with coupling the compound of formula 1 with a compound of formula 8 to obtain a compound of formula 7.

DETAILED DESCRIPTION

One aspect of the invention is a process to prepare compounds of formula 7 wherein L is ethylene; R is $R^1$-fura-nyl, $R^1$-thienyl, $R^1$-pyridyl, $R^1$-pyridyl N-oxide, $R^1$-oxazolyl, $R^{10}$-phenyl, $R^1$-pyrrolyl or cycloalkenyl; $R^1$ is hydrogen or halogen; Y is

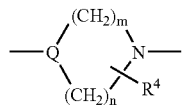

wherein Q is

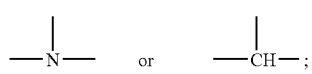

Z is $R^5$-phenyl, $R^5$-heteroaryl, $R^6$—C(O)— or $R^6$—SO$_2$—; and $R^6$ is $R^5$-phenyl.

Another aspect of the invention is a process to prepare compounds of formula 7 wherein R is $R^1$-furanyl; $R^1$ is hydrogen or halogen; Q is

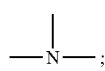

m and n are each 2; $R^4$ is hydrogen; Z is $R^5$-phenyl; and $R^5$ is one substituent selected from the group consisting of alkoxy and alkoxyalkoxy.

Another aspect of the invention is a process to prepare compounds of formula 7 wherein A is chlorine or bromine.

Another aspect of the invention is a process to prepare compounds of formula 7 wherein the compound of formula HO-L-NHNH$_2$ is 2-hydroxyethylhydrazine.

Another aspect of the invention is a process to prepare compounds of formula 7 wherein the dehydrating agent is P$_2$O$_5$ or POCl$_3$, preferably POCl$_3$.

Another aspect of the invention is a process to prepare compounds of formula 7 the dehydrating agent is POCl$_3$ and the metal halide is ZnBr$_2$.

Another aspect of the invention is a process to prepare compounds of formula 7 wherein R is $R^1$-furanyl, $R^1$ is hydrogen, Z is $R^5$-phenyl and $R^5$ is methoxyethoxy.

Another aspect of the invention is a process to prepare compounds of formula 7 wherein the dehydrating agent is P$_2$O$_5$ and the halide salt is NaCl.

Another aspect of the invention is a process to prepare compounds of formula 7A

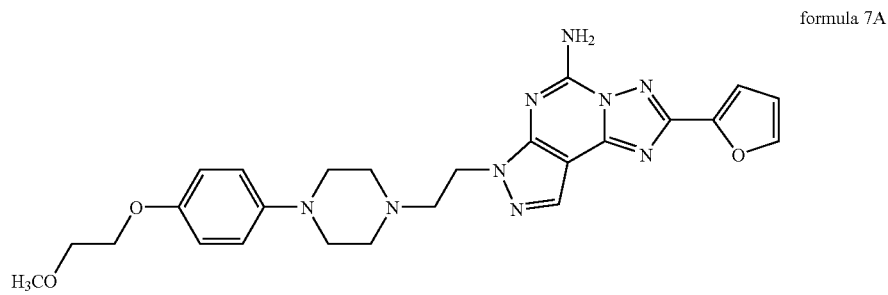

formula 7A or a pharmaceutically acceptable salt or solvate thereof, comprising a) halogenating and formylating a compound of formula 6

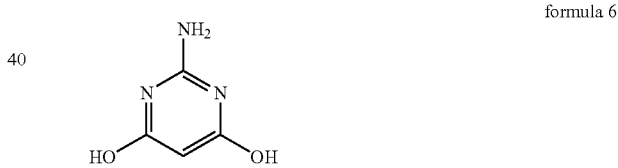

formula 6 to obtain a compound of formula 5A

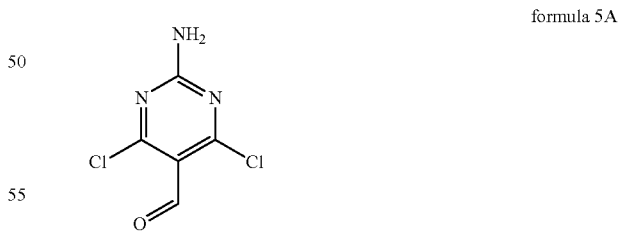

formula 5A (b) coupling the compound of formula 5A with a hydrazine of formula 4A

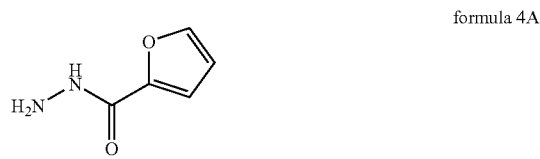

formula 4A in the presence of a base to form a compound of formula 3A

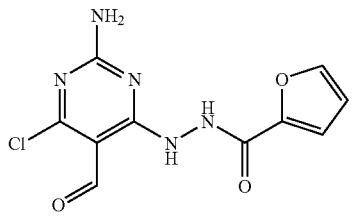

formula 3A (c) reacting the compound of formula 3A with 2-hydroxy-ethyl hydrazine to form a compound of formula 2A

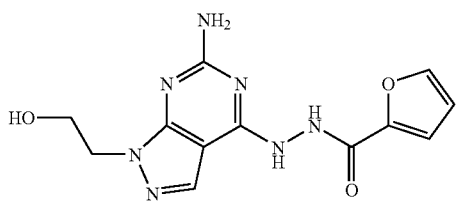

formula 2A (d) concurrently (1) cyclizing and (2) halogenating the compound of formula 2A by reacting the compound of formula 2A in the presence of catalytic amount of a metal halide or a catalytic amount of a halide salt and a dehydrating agent to form a compound of formula 1A

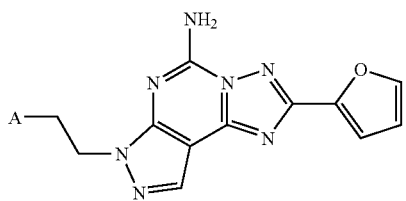

formula 1A wherein A is halogen and (e) preparing the compound of formula 7A by coupling the compound of formula 1A with a compound of formula 8A

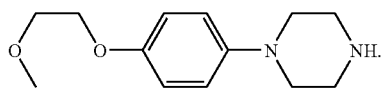

formula 8A in the presence of a base. Preferably, in the process of forming a compound of formula 7A, the metal halide is $ZnBr_2$ and the dehydrating agent is $POCl_3$. Alternatively, the cyclization and halogentation of formula 2A takes place in the presence of NaCl and $P_2O_5$.

An additional aspect of the invention is a process to prepare compounds of formula 1

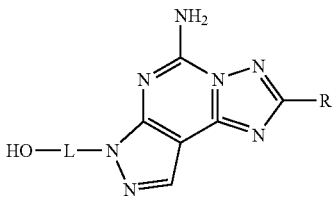

formula 1 wherein
L is alkylene;
R is aryl, heteroaryl, $R^1$-aryl, $R^1$-heteroaryl or cycloalkenyl;
$R^1$ is 1 to 3 substituents independently selected from the group consisting of hydrogen, alkyl, —$CF_3$, halogen, —$NO_2$, —$NR^{12}R^{13}$, alkoxy, alkylthio, alkylsulfinyl, and alkylsulfonyl;
and
$R^{10}$ is 1 to 5 substituents independently selected from the group consisting of hydrogen, halogen, alkyl, hydroxy, alkoxy, —CN, —$NH_2$, alkylamino, dialkylamino, —$CF_3$, —$OCF_3$ and —$S(O)_{0-2}$alkyl;
comprising concurrently (1) cyclizing and (2) halogenating the compound of formula 2

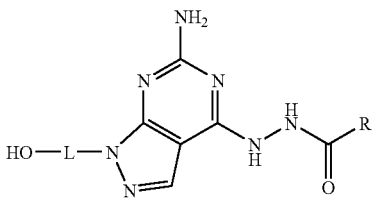

formula 2 by reacting the compound of formula 2 in the presence of catalytic amount of a metal halide or a catalytic amount of a halide salt and dehydrating agent to form a compound of formula 1.

An additional aspect of the invention is a process to prepare compounds of formula 1 wherein the dehydrating agent is a phosphorous oxyhalide; preferably either $P_2O_5$ or $POCl_3$.

In an additional aspect of the invention is a process to prepare compounds of formula 1 wherein the dehydrating agent is $POCl_3$ and the metal halide is zinc halide, preferably, $ZnBr_2$. Alternatively, an additional aspect of the invention is a process to prepare compounds of formula 1 wherein the halide salt is NaCl and the dehydrating agent is $P_2O_5$.

The claimed process produces compounds of formula 7 which can have A2a receptor antagonistic activity, as well as those intermediate compounds used to produce compounds of formula 7.

In step (a), the compound of formula 6 is converted into a compound of formula 5. Typically, said conversion takes place in the presence of a phosphorous oxyhalide such as $POCl_3$, a solvent such as DMF or DME and at temperature of about 95° C. to about 105° C., preferably about 100° C. In step (a) $POCl_3$ is a halogenating agent, however, it can be used as a dehydrating agent as later demonstrated in step (d).

In step (b), the compound of formula 5 is coupled with a hydrazine of formula 4, to form a compound of formula 3. The reaction is carried out in a non-protic organic solvent such as CH₃CN, and an inorganic base or organic base, at a temperature of about 1° C. to about 100° C., more preferably at a temperature of about 20° C. to about 80° C., even more preferably about 30° C. to about 50° C., most preferably at about 40° C. Examples of suitable inorganic bases are Na₂CO₃, NaHCO₃, KHCO₃, NaOH, KOH, K₃PO₄, K₂HPO₄, Na₃PO₄ and Na₂HPO₄. Examples of suitable organic bases include but are not limited to, triethylamine, DBU, pyridine and DIEA. Further, aprotic solvents such as THF and toluene, etc. could also replace acetonitrile in this reaction.

About 1-2 equivalents, preferably about 1 equivalent, of a compound of formula 5 are used, and about 1-2, preferably about 1-1.1 equivalents of the hydrazine of formula 4. Preferably, about 1 equivalent of the inorganic base is used. Preferably, the activated compound of formula 3 is not isolated before the reaction.

In step (c), the compound of formula 3 is reacted with a compound of HO-L-NHNH₂, to form a compound of formula 2. Preferably, L is ethylene. The reaction is carried out in the presence of a non-protic organic base and/or inorganic base (see above), at a temperature range of 30° C. to about 12° C., preferably at about 50° C. to about 100° C., even more preferably at about 70 to 90° C., most preferably at about 80° C. About 2 equivalents of the hydroxy alkyl hydrazine are used.

In step (d), the compound of formula 2 is obtained by concurrently (1) cyclizing and (2) halogenating the compound of formula 2 by reacting the compound of formula 2 in the presence of catalytic amount of a metal halide and dehydrating agent or a catalytic amount of a halide salt and dehydrating agent to form a compound of formula 1, which may be, but are not limited to, the following formulas:

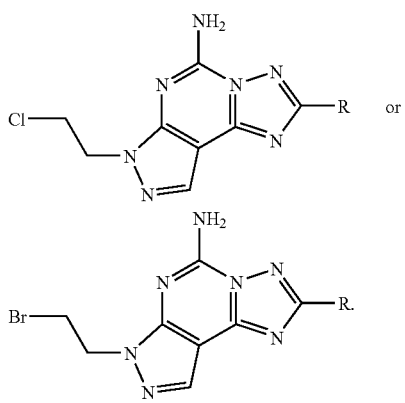

While step (d) has been described as a concurrent halogenation and cyclization of the compound of formula 2, modifications, such as a separate 2-step process where halogenation and cyclization occur as separate steps, are intended to fall within the spirit and scope of the present invention.

The reaction is carried out in an organic solvent such as toluene at a temperature range of about 80° C. to about 120° C., more preferably 90° C. to about 110° C., most preferably 100° C. and then subsequently cooled and quenched to a temperature of about 0° C.

Specific examples of metal halides include but are not limited to FeCl₃, AlCl₃, ZnCl₂, and ZnBr2. A combination of a phosphorous oxy compound and a metal salt (e.g. P₂O₅ and NaCl), also resulted in the desired product.

In step (e), the compound of formula 7 is formed by coupling the compound of formula 1 with a compound of formula 8 in the presence of a base. Preferred examples of bases include but are not limited to amines, more preferably alkylamines, even more preferably trialkylamines, most preferably diisopropylethyl amide. The reaction is carried out with an aprotic organic solvent, (such as DMF, acetonitrile, toluene, THF, etc.), at temperature range of about 50 to about 120° C., preferably at 65 to 100° C., more preferably at 75 to 85° C., most preferably at 80° C. The reaction mixture is cooled in an ice water bath to about 0° C., and stirred (preferably for 2 hours). The resulting solid is filtered, washed (e.g. with a solution acetonitrile and water) and dried to yield the product, a compound of formula 7.

The present process provides an advantage over the procedures previously reported in the art. Known processes used highly toxic and corrosive NH₂CN to form the six membered heteroaryl of the final product. The presently claimed process avoids this cyclization step altogether by using a starting material (a compound of formula 6) that already has a six membered ring. The compound of formula 6 is further processed by the claimed invention to yield the final product, compounds of formula 7. The present invention avoids the use of toxic cyanogen halides, which in turn, therefore, allows for large scale production and high yields using milder conditions.

As used herein, "alkyl" means an aliphatic hydrocarbon group, which may be straight or branched and comprising about 1 to about 6 carbon atoms in the chain. Branched means that one or more lower alkyl groups such as methyl, ethyl or propyl, are attached to a linear alkyl chain. Alkylene, referring to a divalent alkyl group, similarly refers to straight or branched chains.

"Alkoxy" means an alkyl-O-group in which the alkyl group is as previously described, unless otherwise noted. Non-limiting examples of suitable alkoxy groups include methoxy, ethoxy, n-propoxy, isopropoxy, n-butoxy and heptoxy. The bond to the parent moiety is through the ether oxygen.

"Cycloalkyl" means a non-aromatic ring system comprising about 3 to about 6 carbon atoms. Non-limiting examples of suitable monocyclic cycloalkyls include cyclopropyl, cyclopentyl and cyclohexyl, and the like. Cycloalkylene refers to a divalent cycloalkyl group. Cycloalkenyl refers to a C₄–C₆ cycloalkyl ring comprising one double bond. R¹ or R⁵-substituted cycloalkyl refers to such groups wherein substitutable ring carbon atoms have a substituent as defined above.

"Heteroaryl" means a single ring, bicyclic or benzofused heteroaromatic group of 5 to 10 atoms comprised of 2 to 9 carbon atoms and 1 to 4 heteroatoms independently selected from the group consisting of N, O and S, provided that the rings do not include adjacent oxygen and/or sulfur atoms. N-oxides of the ring nitrogens are also included. Examples of single-ring heteroaryl groups are pyridyl, pyridyl N-oxide oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of bicyclic heteroaryl groups are naphthyridyl (e.g., 1, 5 or 1,7), imidazopyridyl, pyrido[2,3]imidazolyl, pyridopyrimidinyl and 7-azaindolyl. Examples of benzofused heteroaryl groups are indolyl, quinolyl, isoquinolyl, phthalazinyl, benzothienyl (i.e., thionaphthenyl), benzimidazolyl, benzofuranyl, benzoxazolyl and benzofurazanyl. All positional isomers are contemplated, e.g., 2-pyridyl, 3-pyridyl and 4-pyridyl. R¹ or R⁵-substituted heteroaryl refers to such groups wherein substitutable ring carbon atoms have a substituent as defined above.

"Alkylthio" means an alkyl-S-group in which the alkyl group is as previously described. Non-limiting examples of suitable alkylthio groups include methylthio, ethylthio, and i-propylthio. The bond to the parent moiety is through the sulfur.

"Alkylsulfonyl" means an alkyl-S($O_2$)—group. The bond to the parent moiety is through the sulfonyl.

"Alkylsulfinyl" means an alkyl-S(O)—group. The bond to the parent moiety is through the sulfinyl.

"Carbonyl" means a —C(O)—moiety, e.g., alkoxycarbonyl refers to an alkoxy-C(O)-group (i.e., alkyl-O—C(O)—).

"Acetyl" means —C(O)$CH_3$.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Certain compounds of the invention may exist in different stereoisomeric forms (e.g., enantiomers, diastereoisomers and atropisomers). The invention contemplates all such stereoisomers both in pure form and in mixture, including racemic mixtures.

Certain compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Following are descriptions of the preparation of compounds of formula 7 using the claimed process.

The following abbreviations are used in the specification and claims: Ms (methylsulfonyl); Me (methyl); et or Et (ethyl); THF (tetrahydrofuran); LOD (loss on drying); diisopropylethyl amine (DIEA); DMF (dimethylformide); DBU (1, 8 diazabicyclo[5.4.0]undec-7-ene); (DME) 1,2-dimethoxyethane; and DMSO (dimethyl sulfoxide).

General Scheme

The below scheme outlines the claimed process starting material, a compound of formula 6, until the final step where a compound of formula 1 is coupled with a couple of formula to produce the final product, a compound of formula 7.

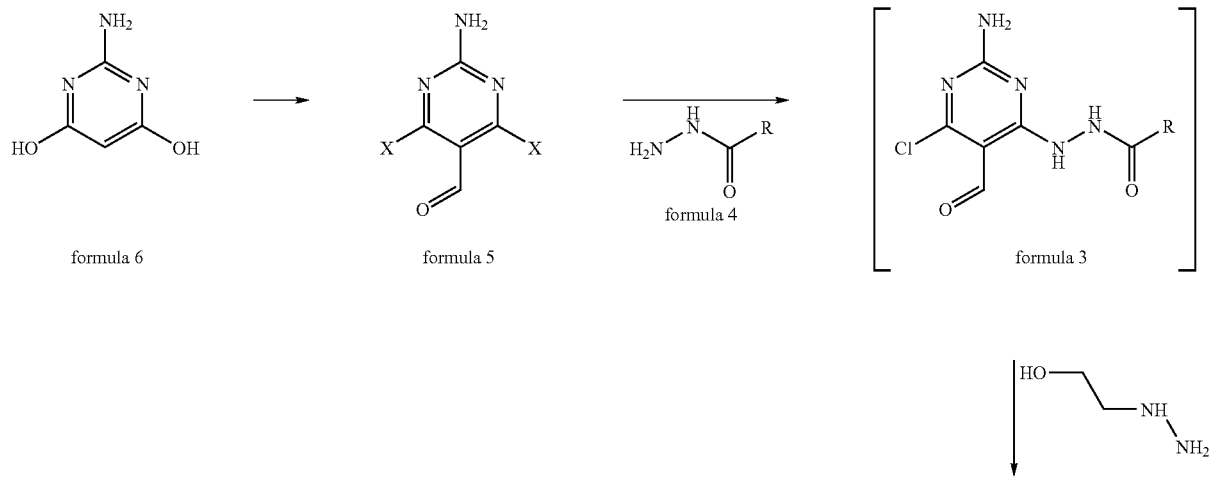

-continued

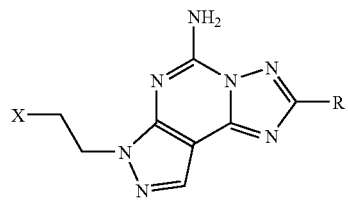
X = Br/Cl
formula 1

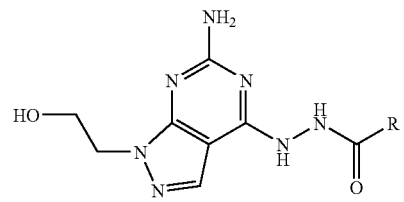
formula 2

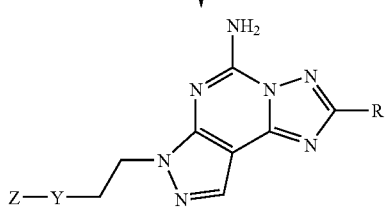
formula 7

Z—Y—H
formula 8

1. Formation of Compound for formula 5:

Initially, a compound of formula 6 was reacted with $POCl_3$ in DMF and heat to form a compound of formula 5.

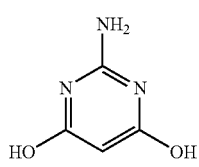  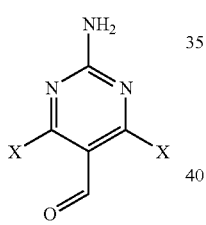

formula 6                    formula 5

The compound of formula 5 subsequently treated, (details below) to practice the process of the claimed invention. As seen below, a compound of formula 5, wherein X is chloride, is subsequently reacted to form an intermediate compound of formula II.

2. Procedures for preparation of compound II

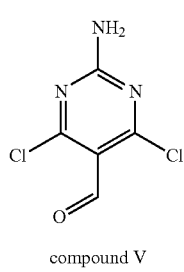

compound V

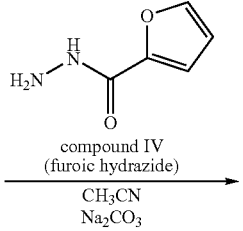

compound IV
(furoic hydrazide)
$CH_3CN$
$Na_2CO_3$
40 Deg. C

-continued

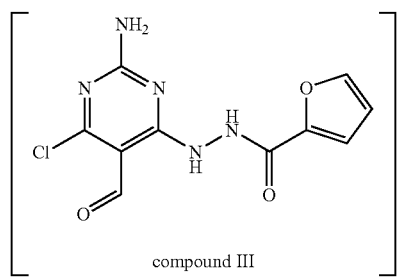

compound III

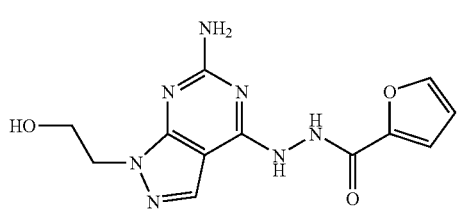

compound II

Compound V (1.0 g, 1.0 eq.), 2-furoic hydrazide (0.7 g, 1.1 eq.) and sodium carbonate (0.55 g, 1.0 eq.) were added acetonitrile (20 mL) and was heated to 40° C. After stirring at 40° C. for 30 hours, the reaction was subsequently heated to 60° C. A solution of 2-hydroxyethyl hydrazine (0.7 mL, 2 eq.) in water (5mL) was added. The reaction mixture was then heated to 80° C. and stirred for 2.5 hours. Once the reaction was completed, the reaction mixture was cooled down to 25° C., and 0.1 N HCl (10 mL) was added. The reaction mixture was stirred at 25° C. for 2 hours. The reaction mixture was then concentrated to about 10 mL under reduced pressure. Water (30 mL) was added and the reaction mixture was concentrated to about 10 mL under reduced pressure. The reaction mixture was stirred at 25° C. for overnight. The solid was filtered and washed with 2 mL water, then with 2 mL acetonitrile. The product (compound I) was dried under vacuum at 25° C. to yield 1.1 g (70%) of the desired product. LC/MS: m/z=304 (M+1) $^1$H NMR (DMSO-$d_6$): δ 10.65 (d, 1H); 9.52 (d, 1H); 7.98–7.88 (m,1 H); 7.42–7.29 (m, 1 H); 6.73–6.70 (m,1 H); 6.35 (s, 2H); 4.1 (m, 2H); 3.62 (m, 2H)

A mixture of Intermediate compound II (500 mg, 1.0 eq.), Zinc Bromide (100 mg) and POCl$_3$ (5 ml) was heated to 100° C. and stirred for 6 hours. After the reaction completion, the reaction mixture was then cooled down to 0° C., and ice cold water (15 ml) was slowly added to quench the reaction. The resulting solid was filtered, washed with water and dried to give 420 mg of the product, compound I (as a bromide and chloride mixture).

Mass spectrum: M+1=304 (X=Cl); M+1=348 (X=Br). $^1$HNMR (DMSO): 8.37 (s, 1H), 8.26 (bs, 2H), 7.95 (m, 1H), 7.24 (m, 1H), 6.74 (m, 1H), 4.60 (m, 2H), 4.05 (m, 2H), 3.48 (m, 4H)

4. Procedures for preparation of compound VII:

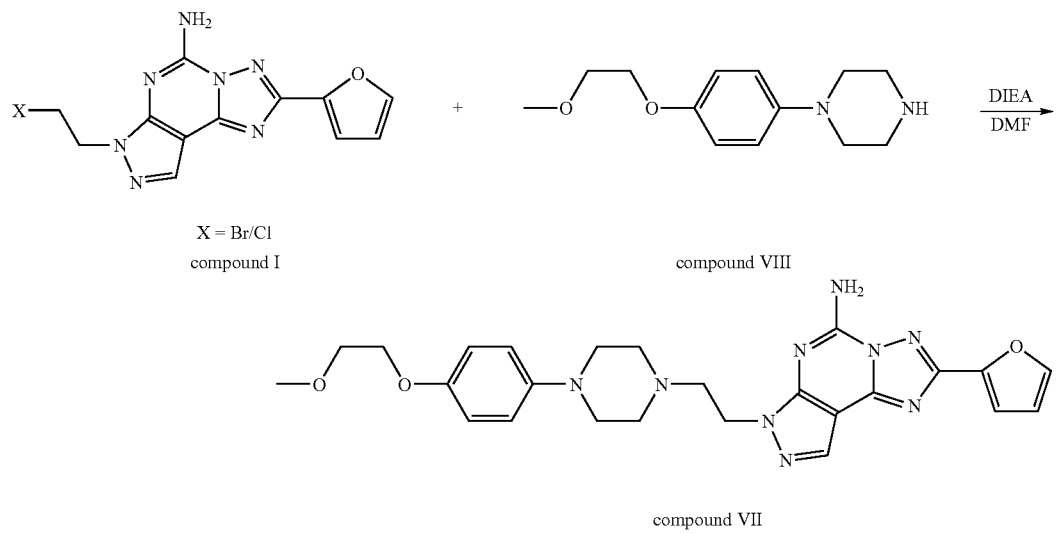

3. Procedures for preparation of compound I.

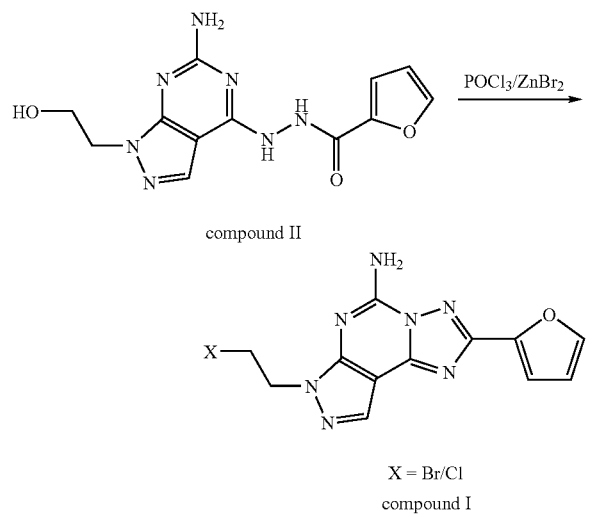

A mixture of compound 1, (900 mg, 1.0 eq.), compound VIII ( (1.2 g, 2.0 eq) and diisopropylethyl amine (DIEA) (1.5 ml, 4.5 eq.) in dimethylformide (DMF) (7.2 ml) was heated to 80° C. and stirred for 10 hours. After the reaction completion, the reaction mixture was then cooled down in an ice-water bath to 0° C., and stirred for 2 hours. The resulting solid was filtered, washed with acetonitrile, water and dried to give 870 mg of the product, compound VII. Mass spectrum: M+1=504; $^1$HNMR (DMSO): 8.37 (s, 1H), 8.13 (bs, 2H), 7.95 (m, 1H), 7.18 (m, 1H), 6.78 (m, 4H), 6.70 (m, 1H), 4.38 (m, 2H), 4.93(m, 2H), 3.56 (m, 2H), 3.37 (s, 3H), 2.90 (m, 4H), 2.80 (m, 2H), 2.55 (m, 4H), 2.45 (m, 2H).

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:
1. A process for preparing compounds of formula 7

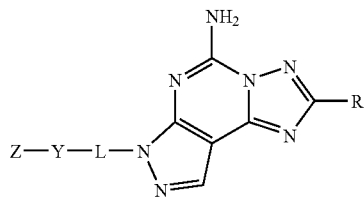
formula 7 or a pharmaceutically acceptable salt thereof, wherein;
L is alkylene;
R is aryl, heteroaryl, $R^1$-aryl, $R^1$-heteroaryl or cycloalkenyl;
Y is —N($R^2$)$CH_2CH_2$N($R^3$)—, —$OCH_2CH_2$N($R^2$)—, —($CH_2$)$_2$—NH—, or

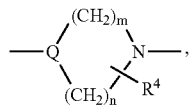

and
Z is aryl, $R^5$-aryl, aralkyl, $R^5$-aralkyl, heteroaryl, $R^5$-heteroaryl, (aryl)$_2$alkyl-, $R^6$—C(O)—, $R^6$—$SO_2$—,

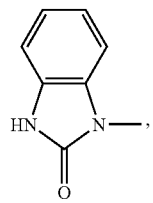

$R^5$-aryl-CH(OH)— or aryl-CH(OH)—; or when Q is

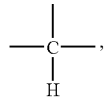

Z is also phenylamino or pyridylamino;
or
Z and Y together are

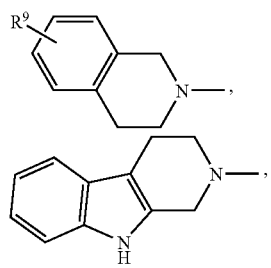

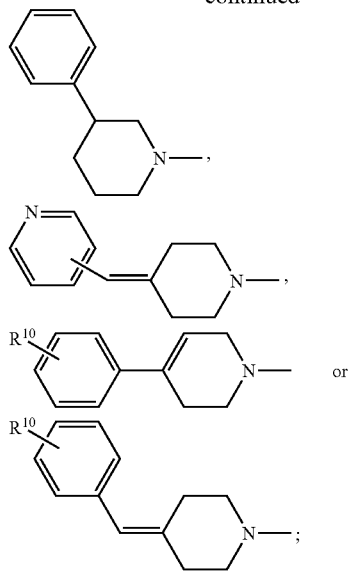

$R^1$ is 1 to 3 substituents independently selected from the group consisting of hydrogen, alkyl, —$CF_3$, halogen, —$NO_2$, —$NR^{12}R^{13}$, alkoxy, alkylthio, alkylsulfinyl, and alkylsulfonyl;
$R^2$ and $R^3$ are independently selected from the group consisting of hydrogen and alkyl;
m and n are each independently 2 or 3;
Q is

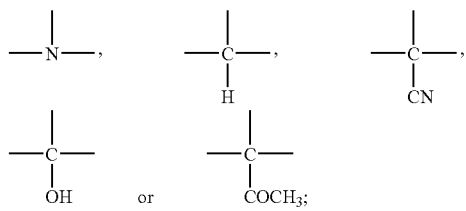

$R^4$ is 1 to 2 substituents independently selected from the group consisting of hydrogen and alkyl, or two $R^4$ substituents on the same carbon can form =O;
$R^5$ is 1 to 5 substituents independently selected from the group consisting of hydrogen, halogen, alkyl, hydroxy, alkoxy, —CN, dialkyl-amino, —$CF_3$, —$OCF_3$, acetyl, —$NO_2$, hydroxyalkoxy, alkoxyalkoxy, dialkoxyalkoxy, alkoxy-alkoxy-alkoxy, carboxy-alkoxy, alkoxycarbonylalkoxy, cycloalkyl-alkoxy, dialkyl-amino-alkoxy, morpholinyl, alkyl-$SO_2$—, alkyl-$SO_2$-alkoxy, tetrahydropyranyloxy, alkylcarbonyl-alkoxy, alkoxycarbonyl, alkylcarbonyloxy-alkoxy, —$SO_2NH_2$, or phenoxy; or adjacent $R^5$ substituents together are —O—$CH_2$—O—, —O—$CH_2CH_2$—O—, —O—$CF_2$—O— or —O—$CF_2CF_2$—O— and form a ring with the carbon atoms to which they are attached;
$R^6$ is alkyl, aryl, $R^5$-aryl, aralkyl, $R^5$-aralkyl, heteroaryl, $R^5$-heteroaryl, $R^5$-cycloalkyl, cycloalkyl, alkyl-OC(O)—NH—($C_1$–$C_6$)alkyl-, dialkyl-aminomethyl or

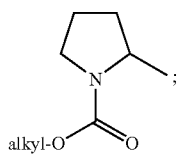

$R^9$ is 1 to 2 substituents independently selected from the group consisting of hydrogen, alkyl, hydroxy, alkoxy, halogen, —$CF_3$ and alkoxy-alkoxy;

$R^{10}$ is 1 to 5 substituents independently selected from the group consisting of hydrogen, halogen, alkyl, hydroxy, alkoxy, —CN, —$NH_2$, alkylamino, dialkylamino, —$CF_3$, —$OCF_3$ and —$S(O)_{0-2}$alkyl;

$R^{12}$ is hydrogen or alkyl;

and $R^{13}$ is alkyl-C(O)— or alkyl-$SO_2$—;

comprising a) halogenating and formylating a compound of formula 6

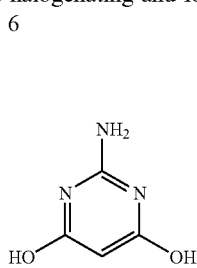

formula 6 to obtain a compound of formula 5

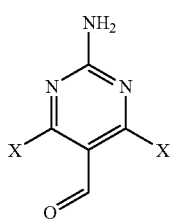

formula 5 wherein X is halogen (b) coupling the compound of formula 5 with a hydrazine of formula 4

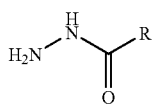

formula 4 in the presence of a base to form a compound of formula 3

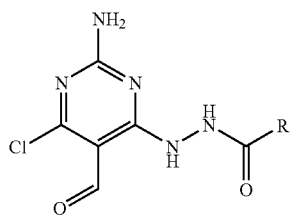

formula 3

(c) reacting the compound of formula 3 with a compound of formula HO-L-$NHNH_2$ to form a compound of formula 2

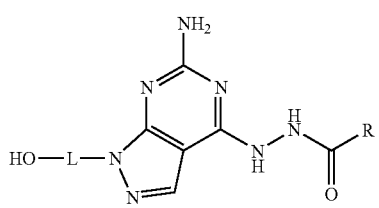

formula 2

(d) concurrently (1) cyclizing and (2) halogenating the compound of formula 2 by reacting the compound of formula 2 in the presence of catalytic amount of a metal halide or a catalytic amount of a halide salt and a dehydrating agent to form a compound of formula 1

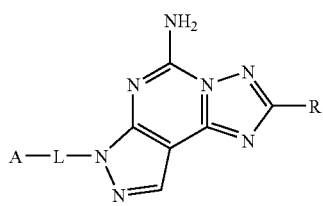

formula 1 wherein A is halogen;
and (e) preparing the compound of formula 7 by coupling the compound of formula 1 with a compound of formula 8

Z-Y—H      formula 8 in the presence of a base.

2. The process of claim 1 for preparing compounds of formula 7 wherein:

L is ethylene;

R is $R^1$-furanyl, $R^1$-thienyl, $R^1$-pyridyl, $R^1$-pyridyl N-oxide, $R^1$-oxazolyl, $R^{10}$-phenyl, $R^1$-pyrrolyl or cycloalkenyl;

$R^1$ is hydrogen or halogen;

Y is

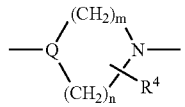

wherein Q is

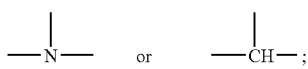

Z is $R^5$-phenyl, $R^5$-heteroaryl, $R^6$—C(O)— or $R^6$—SO$_2$—;

and
$R^6$ is $R^5$-phenyl.

3. The process of claim 2 wherein
R is $R^1$-furanyl;
$R^1$ is hydrogen or halogen;
Q is

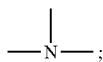

m and n are each 2;
$R^4$ is hydrogen;
Z is $R^5$-phenyl;
and
$R^5$ is one substituent selected from the group consisting of alkoxy and alkoxyalkoxy.

4. The process of claim 1 wherein A is chlorine or bromine.

5. The process of claim 1 wherein X of the compound of formula 5 is Cl.

6. The process of claim 1 wherein the base of step (b) Na$_2$CO$_3$, NaHCO$_3$, KHCO$_3$, NaOH, KOH, K$_3$PO$_4$, K$_2$HPO$_4$, Na$_3$PO$_4$ and Na$_2$HPO$_4$.

7. The process of claim 1 wherein the base of step (b) is Na$_2$CO$_3$.

8. The process of claim 1 wherein the base of step (e) is a trialkylamine.

9. The process of claim 1 wherein the base of step (e) is diisopropylethyl amide.

10. The process of claim 1 wherein the compound of formula HO-L-NHNH$_2$ is 2-hydroxyethylhydrazine.

11. The process of claim 1 wherein the dehydrating agent of step (d) is P$_2$O$_5$ or POCl$_3$.

12. The process of claim 11 wherein the dehydrating agent of step (d) is POCl$_3$ and the metal halide is ZnBr$_2$.

13. The process of claim 1 wherein R is $R^1$-furanyl, $R^1$ is hydrogen, Z is $R^5$-phenyl and $R^5$ is methoxyethoxy.

14. The process of claim 1 wherein the dehydrating agent of step (d) is P$_2$O$_5$.

15. The process of claim 14 wherein the halide salt of step (d) is NaCl.

16. The process of claim 1 for preparing a compound of formula 7A

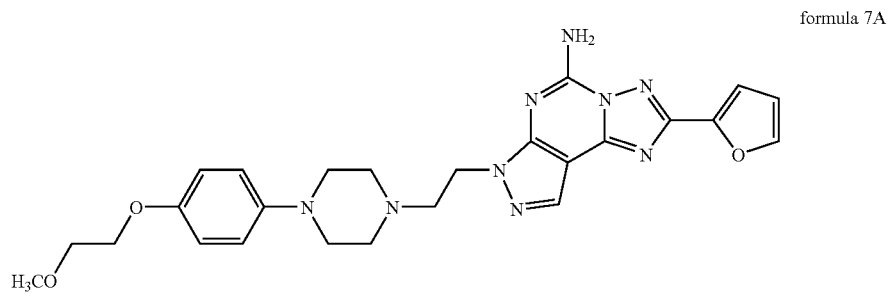

formula 7A or a pharmaceutically acceptable salt thereof, comprising
a) halogenating and formylating a compound of formula 6

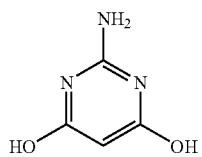

formula 6 to obtain a compound of formula 5A

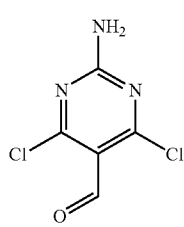

formula 5A (b) coupling the compound of formula 5A with a hydrazine of formula 4A

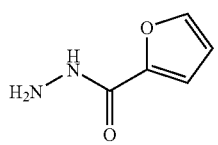

formula 4A in the presence of a base to form a compound of formula 3A

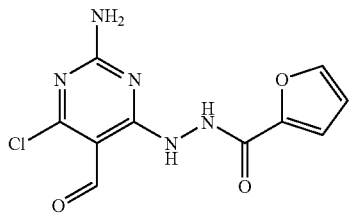
formula 3A (c) reacting the compound of formula 3A with 2-hydroxyethyl hydrazine to form a compound of formula 2A

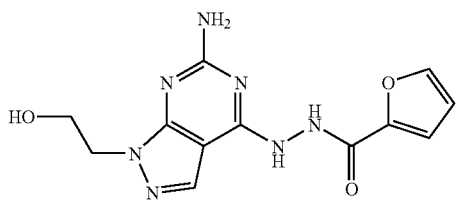
formula 2A (d) concurrently (1) cyclizing and (2) halogenating the compound of formula 2A by reacting the compound of formula 2A in the presence of catalytic amount of a metal halide or a catalytic amount of a halide salt and a dehydrating agent to form a compound of formula 1A

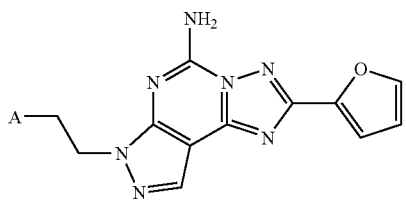
formula 1A wherein A is halogen
and
(e) preparing the compound of formula 7A by coupling the compound of formula 1A with a compound of formula 8A

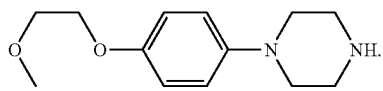
formula 8A in the presence of a base.

17. The process of claim 16 wherein the metal halide is $ZnBr_2$ and the dehydrating agent is $POCl_3$.

18. The process of claim 16 wherein the halide salt is NaCl and the dehydrating agent is $P_2O_5$.

19. A process for preparing compounds of formula 1

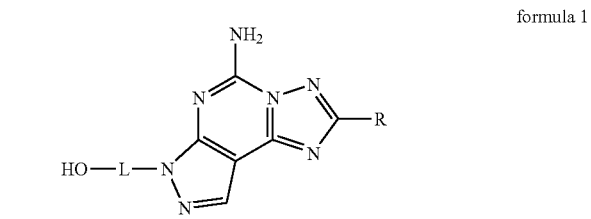
formula 1 wherein
L is alkylene;
R is aryl, heteroaryl, $R^1$-aryl, $R^1$-heteroaryl or cycloalkenyl;
$R^1$ is 1 to 3 substituents independently selected from the group consisting of hydrogen, alkyl, —$CF_3$, halogen, —$NO_2$, —$NR^{12}R^{13}$, alkoxy, alkylthio, alkylsulfinyl, and alkylsulfonyl;
and
$R^{10}$ is 1 to 5 substituents independently selected from the group consisting of hydrogen, halogen, alkyl, hydroxy, alkoxy, —CN, —$NH_2$, alkylamino, dialkylamino, —$CF_3$, —$OCF_3$ and —$S(O)_{0-2}$alkyl;

comprising concurrently (1) cyclizing and (2) halogenating the compound of formula 2

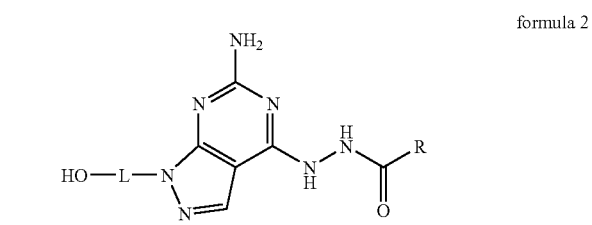
formula 2 by reacting the compound of formula 2 in the presence of catalytic amount of a metal halide or a catalytic amount of a halide salt and dehydrating agent to form a compound of formula 1.

20. The process of claim 19 wherein the dehydrating agent is a phosphorous oxyhalide.

21. The process of claim 20 wherein dehydrating agent is $P_2O_5$ or $POCl_3$.

22. The process of claim 21 wherein the dehydrating agent is $POCl_3$.

23. The process of claim 19 wherein the metal halide is zinc halide.

24. The process of claim 23 wherein the metal halide is $ZnBr_2$.

25. The process of claim 24 wherein the metal halide is $ZnBr_2$ and the dehydrating agent is $POCl_3$.

26. The process of claim 19 wherein the halide salt is NaCl and the dehydrating agent is $P_2O_5$.

* * * * *